US012251251B2

(12) United States Patent
Kimchy et al.

(10) Patent No.: US 12,251,251 B2
(45) Date of Patent: Mar. 18, 2025

(54) RADIATION CAPSULE FOR BOWEL DISEASE IMAGING AND LOCALIZE DRUG DELIVERY

(71) Applicant: CHECK-CAP LTD., Isfiya (IL)

(72) Inventors: Yoav Kimchy, Haifa (IL); Alex Ovadia, Haifa (IL)

(73) Assignee: CHECK-CAP LTD., Isfiya (IL)

( * ) Notice: Subject to any disclaimer, the term of this patent is extended or adjusted under 35 U.S.C. 154(b) by 0 days.

(21) Appl. No.: 17/776,232

(22) PCT Filed: Jan. 5, 2021

(86) PCT No.: PCT/IL2021/050012
§ 371 (c)(1),
(2) Date: May 12, 2022

(87) PCT Pub. No.: WO2021/140504
PCT Pub. Date: Jul. 15, 2021

(65) Prior Publication Data
US 2022/0395242 A1    Dec. 15, 2022

Related U.S. Application Data

(60) Provisional application No. 62/957,335, filed on Jan. 6, 2020.

(51) Int. Cl.
*A61B 6/40*    (2024.01)
*A61B 6/00*    (2024.01)
(Continued)

(52) U.S. Cl.
CPC ............. *A61B 6/4057* (2013.01); *A61B 6/06* (2013.01); *A61B 6/425* (2013.01); *A61B 6/4258* (2013.01);
(Continued)

(58) Field of Classification Search
CPC ......... A61B 6/4057; A61B 6/06; A61B 6/425; A61B 6/4258; A61B 6/4266; A61B 6/485;
(Continued)

(56) References Cited

U.S. PATENT DOCUMENTS

| | | | |
|---|---|---|---|
| 2002/0099310 A1* | 7/2002 | Kimchy | ............... A61B 5/4255 600/587 |
| 2004/0054278 A1* | 3/2004 | Kimchy | ................. A61B 6/425 600/407 |

(Continued)

FOREIGN PATENT DOCUMENTS

CN    110025284 A    7/2019

OTHER PUBLICATIONS

Watne, Alvin L. "Colon polyps." Journal of surgical oncology 66.3 (1997): 207-214. (Year: 1997).*

*Primary Examiner* — Sean D Mattson
(74) *Attorney, Agent, or Firm* — Rimon, P.C.; David I. Greenbaum

(57) ABSTRACT

An imaging capsule including, a radiation source, a collimator that provides a collimated beam from the radiation source, at least one detector configured to detect particles resulting from X-ray fluorescence and/or Compton backscattering in response to the collimated beam to reconstruct images of a user's gastrointestinal tract, wherein the imaging capsule is configured to identify an inflamed area, within the user's gastrointestinal tract, based on a count of the detected particles and initiate actions responsive to detecting the inflamed area.

19 Claims, 3 Drawing Sheets

(51) Int. Cl.
*A61B 6/06* (2006.01)
*A61B 6/42* (2024.01)

(52) U.S. Cl.
CPC ............ *A61B 6/4266* (2013.01); *A61B 6/485* (2013.01); *A61B 6/547* (2013.01)

(58) Field of Classification Search
CPC .. A61B 6/547; A61B 5/01; A61B 5/03; A61B 5/062; A61B 5/14539; A61B 5/4255; A61B 5/06; A61B 2562/0219; A61B 2562/0223; A61K 9/0009

See application file for complete search history.

(56) References Cited

U.S. PATENT DOCUMENTS

| | | | | |
|---|---|---|---|---|
| 2004/0253304 | A1* | 12/2004 | Gross | A61B 5/14539 |
| | | | | 424/451 |
| 2007/0161885 | A1* | 7/2007 | Kimchy | A61B 5/42 |
| | | | | 600/407 |
| 2013/0197360 | A1* | 8/2013 | Baum | A61B 6/4057 |
| | | | | 600/431 |
| 2018/0153497 | A1* | 6/2018 | Gubich | A61B 1/00147 |
| 2018/0154124 | A1* | 6/2018 | Kimchy | A61K 9/0097 |
| 2018/0214104 | A1* | 8/2018 | Kimchy | A61K 49/0065 |

* cited by examiner

RADIATION CAPSULE FOR BOWEL DISEASE IMAGING AND LOCALIZE DRUG DELIVERY

RELATED APPLICATIONS

The present application claims priority from US Provisional application No. 62/957,335 filed on Jan. 6, 2020, the disclosure of which is incorporated herein by reference.

FIELD OF THE INVENTION

The present disclosure relates generally to a system and method which utilizes a radiation based imaging capsule to diagnose and treat the small bowel and the colon for inflammation and disease.

BACKGROUND OF THE INVENTION

Radiation based imaging capsules can be used to perform Colorectal Cancer (CRC) screening within a user's gastrointestinal tract. The imaging capsule typically uses X-ray radiation or Gama-ray radiation to detect polyps, lesions and cancer in the user's colon. The imaging capsule detects changes in morphology of the colon by measuring the distances from the capsule to the colon wall and reconstructing 2D or 3D images of the colon walls.

Typically, the imaging capsule records the measurements and transmits them (e.g. a count rate detected by a particle detector) to an external analysis device, for example a computer or other dedicated instruments for analysis and reconstruction of an image of the inner wall of the colon and/or small intestine.

The imaging capsule may also incorporate a tracking system to identify the location of the imaging capsule as it traverses the gastrointestinal tract and enable reconstruction of a 2D or 3D map with the images of the colon and/or small intestine.

The imaging capsule may also be used to deliver medication to selected positions within the gastrointestinal tract based on position determination and/or real-time images. The medication may be used to provide localized treatments for small bowel cancer, imitable bowel disease (IBD). Crohn's disease and other ailments.

It is of interest to introduce methods of accurately identifying inflamed areas relative to non-inflamed areas to enhance accuracy in treating necessary positions.

SUMMARY OF THE INVENTION

An aspect of an embodiment of the invention, relates to an imaging capsule for scanning with radiation within the gastrointestinal tract of the user, wherein the imaging capsule identifies in which organ it is located based on measurements of sensors in the imaging capsule. Additionally, the imaging capsule is configured to identify an inflamed area based on measurements of the detectors in the imaging capsule. For example based on Compton backscattering counts, which are proportional to the density of the surrounding tissue. Alternatively or additionally, the imaging capsule is configured to detect the inflamed area based on detection of radiation from radioactively labeled tissue of the inflamed area.

In an embodiment of the disclosure, upon detecting an inflamed area the imaging capsule scans the area and provides information to reconstruct images of the area. Alternatively or additionally, the imaging capsule releases medication at the location of the inflamed area.

There is thus provided according to an embodiment of the disclosure, an imaging capsule, comprising:
A radiation source;
A collimator that provides a collimated beam from the radiation source;
At least one detector configured to detect particles resulting from X-ray fluorescence and/or Compton backscattering in response to the collimated beam to reconstruct images of a user's gastrointestinal tract;
Wherein the imaging capsule is configured to identify an inflamed area, within the user's gastrointestinal tract, based on a count of the detected particles and initiate actions responsive to detecting the inflamed area.

In an embodiment of the disclosure, the imaging capsule is further configured to identify the inflamed area based on detecting radiation from radioactively labeled tissue at the inflamed area. Optionally, the initiated actions include releasing medication responsive to detecting the area.

In an embodiment of the disclosure, the initiated actions include taking images of the identified area. Optionally, the imaging capsule further includes one or more sensors configured to identify an approximate location of the imaging capsule.

In an embodiment of the disclosure, the approximate location includes identifying an organ in which the imaging capsule is located. Optionally, the sensors include a pH sensor or a temperature sensor.

In an embodiment of the disclosure, the sensors include a pressure sensor or accelerometer. Optionally, the measurements of the detector are used to identify an approximate location of the imaging capsule based on the distance to the walls surrounding the imaging capsule.

In an embodiment of the disclosure, the measurements of the detector are used to identify an approximate location of the imaging capsule based on an increase or decrease in X-ray fluorescence measurements. Optionally, the imaging capsule is configured to receive coordinates from an external recorder that recorded coordinates from a previously used imaging capsule; and release medication or form images at the location designated by the coordinates.

In an embodiment of the disclosure, the imaging capsule is configured to detect an inflamed area based on Compton backscattering counts, which are proportional to a density of the surrounding tissue.

There is further provided according to an embodiment of the disclosure, a method of using an imaging capsule, comprising:
Receiving an imaging capsule, including a radiation source within a collimator, which provides a collimated beam from the radiation source, and further includes a detector configured to detect particles resulting from X-ray fluorescence and/or Compton backscattering in response to the collimated beam;
Identifying an inflamed area, within the user's gastrointestinal tract, based on a count of the detected particles; and
Initiating actions responsive to detecting the inflamed area.

There is further provided according to an embodiment of the disclosure, an imaging capsule, comprising:
At least one detector configured to detect radiation;
Wherein the imaging capsule is configured to identify an inflamed area while traversing a user's gastrointestinal tract based on detecting radiation from radioactively labeled tissue at the inflamed area

BRIEF DESCRIPTION OF THE DRAWINGS

The present invention will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

The current disclosure relates to a radiation based capsule that enables diagnosis, treatment and follow up monitoring of inflammation in the small bowel, colon or other areas in the gastrointestinal tract. The inflammation is a symptom of various gastrointestinal diseases including cancer. Inflamed tissue may be identified using Compton backscattering that can serve as an indication for tissue thickness which is correlated to the inflammation. Another method uses radiolabeled white blood cells and radiation detection capability to locate inflammation in the vicinity of the inflammation.

Figure 1:
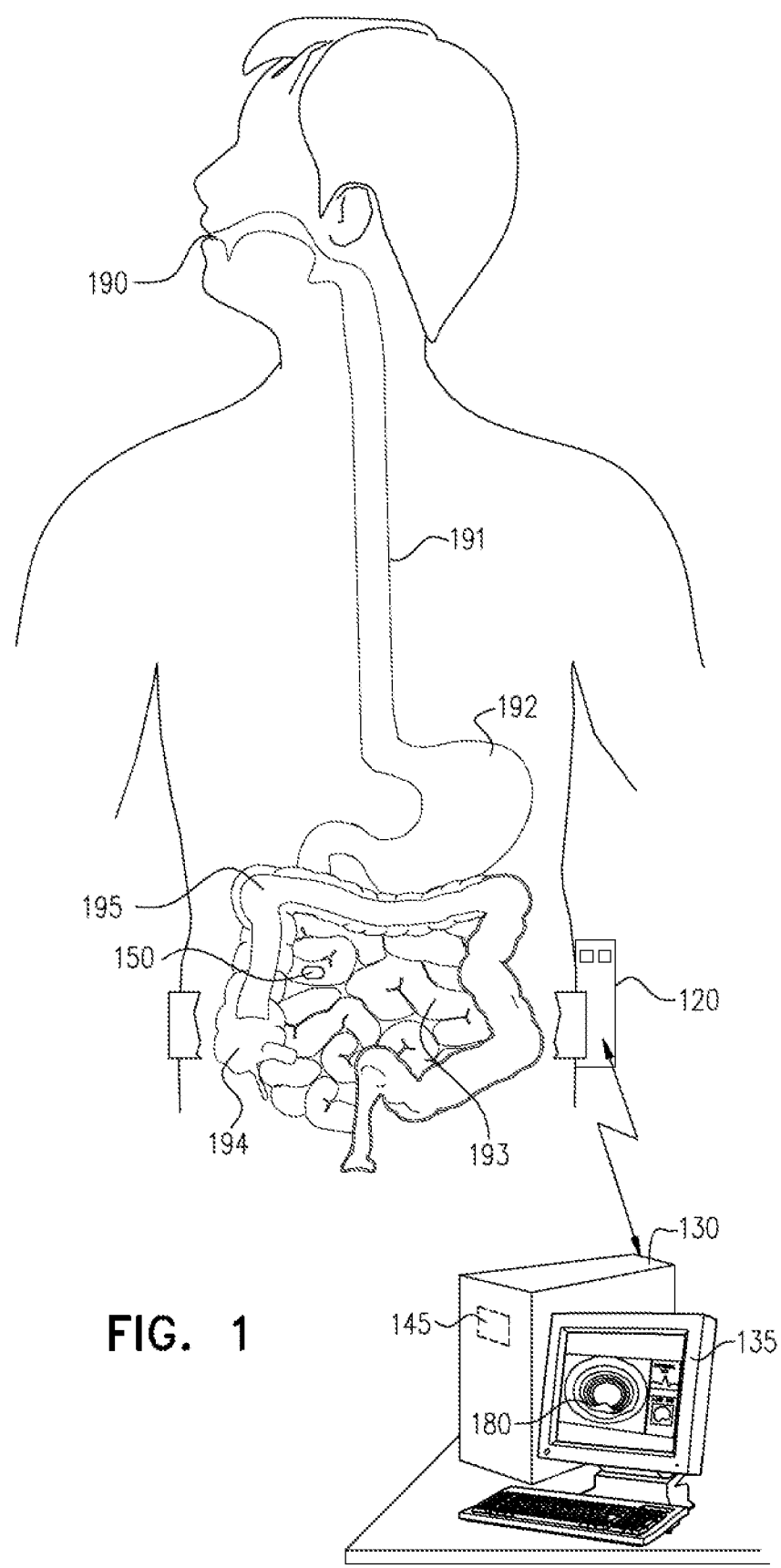
FIG. 1 is a schematic illustration of a system for examining within the gastrointestinal tract, according to an embodiment of the disclosure.

FIG. 1 is a schematic illustration of a system for examining within the gastrointestinal tract of a user, according to an embodiment of the disclosure. Optionally, the user swallows a radio opaque contrast agent solution 160 (e.g. based on Barium or Iodine). The radio opaque contrast agent solution 160 is mixed with the content of the gastrointestinal tract to increase the accuracy of the measurements performed by a radiation based imaging capsule 150. Typically the user waits a few hours (e.g. between 2-8 hours) after swallowing the radio opaque contrast agent solution 160 before swallowing the imaging capsule 150 so that the contrast agent solution 160 will spread through the gastrointestinal tract.

In an embodiment of the disclosure, the imaging capsule 150 travels through the patient's mouth 190, esophagus 191, stomach 192, small intestine (bowel) 193 and then enters the cecum 194, which is the beginning of the colon 195. Then the imaging capsule 150 passes through the colon 195 and exits through the rectum and anus. In an embodiment of the disclosure, the imaging capsule 150 identifies its location (e.g. in which organ it is located and/or where it is located within the organ) based on measurements performed by various sensors in the imaging capsule 150. The imaging capsule 150 takes actions based on its location. Usually to examine the small intestine 193 and/or colon 195. Optionally, the imaging capsule further uses sensors to identify an inflamed area 164 (FIG. 2) to accurately apply treatment.

In an embodiment of the disclosure, the imaging capsule 150 is configured to scan an inner circumference of the walls surrounding it and transmit measurements (e.g. a count rate of particles having specific energies or range of energies) to an external receiver 120 that is typically positioned on the body of the user in the vicinity of the gastrointestinal tract. The external receiver 120 may analyze the information or record the information on a memory card (e.g. SD card) for later analysis. Alternatively or additionally, the receiver 120 may transmit the information to a computer 130 for analysis, for example with an analysis program 145. Optionally, the program 145 may reconstruct an image 180 of the surroundings of the imaging capsule 150. The computer 130 may display the reconstructed image 180 on a screen 135 and/or provide instructions in real time to the imaging capsule 150, for example to release medication or take additional images.

Figure 2:
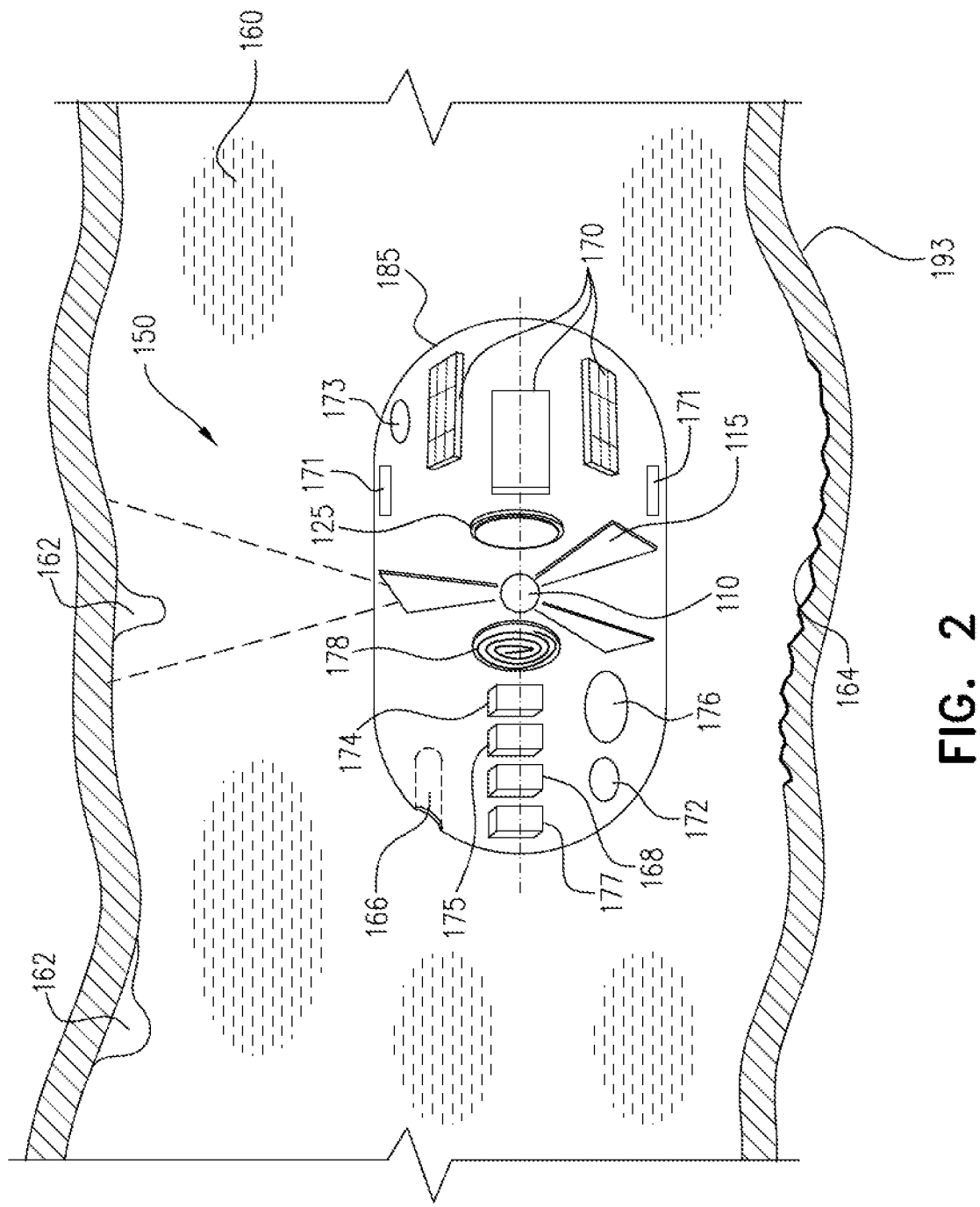
FIG. 2 is a schematic illustration of an imaging capsule in a user's small intestine or colon, according to an embodiment of the disclosure.

FIG. 2 is a schematic illustration of an imaging capsule 150 in a user's small intestine 193 or colon 195, according to an embodiment of the disclosure. In an embodiment of the disclosure, imaging capsule 150 emits radiation (e.g. X-ray or Gamma radiation) from a radiation source 110 through collimators 115 to examine the surroundings of the imaging capsule 150. Optionally, the capsule includes one or more detectors 170 to detect particles reflected in response to the radiation emitted from the radiation source 110. The reflected particles are generally due to Compton backscattering (CNT) from the tissue of the surrounding walls and/or X-ray fluorescence (XMT) from the contrast agent solution 160 mixed with the contents of the small intestine 193 or colon 195. For example, the contrast agent solution 160 travels through the small intestine 193 and adheres to the content and surrounding walls. The imaging capsule 150 is typically swallowed 2-8 hours after swallowing the contrast agent solution 160.

In an embodiment of the disclosure, the detectors are configured to detect and count particles only from specific energy ranges. Thus a certain energy range is identified as CMT particles from human tissue and another energy range is identified as particles from XRF of the contrast agent.

In an embodiment of the disclosure, the imaging capsule 150 senses when it departs from the stomach 192 to the small intestine 193 by using a pH sensor 172 on an enclosure 185 of the imaging capsule 150. The pH sensor 172, senses the change in acidity, from a high acidity in the stomach 192 (pH 1-3 typically) to lower acidity in the small intestine 193 (typically pH 5-7). Optionally, the pH sensor 172 may also identify other organs (e.g. colon 195).

Alternatively or additionally, the imaging capsule 150 may scan with radiation from time to time as it advances, to measure the diameter surrounding it and reconstruct images 180. In the stomach 192, the distance to the walls will be in the order of a few centimeters at least in some of the directions around the capsule. In contrast in the small intestine 193, it will be no more than a few millimeters at the most in all directions. Also, the amount of contrast agent solution 160 in the stomach 192 is expected to be much higher than in the small intestine 193, hence higher XRF measurements are expected. Alternatively or additionally, the capsule may sense the rhythmic bowel movements of the small intestine 193 with an accelerometer 174 and/or pressure sensor 176 to help detection of entrance into the small intestine 193. Alternatively or additionally, hydrostatic pressure around the capsule may provide an indication of the location of the imaging capsule 150, since for example the hydrostatic pressure inside the capsule increases when gasses in the colon diffuse into the capsule, creating a higher internal pressure in the capsule when it in the colon 195 than in the small intestine 193 or the stomach 192.

Thus for example the location of the imaging capsule 150 may be determined based on a pH sensor 172, reconstructed images 180, XRF measurements, a pressure sensors 176, an accelerometer 174 and/or other sensors or a combination thereof.

In an embodiment of the disclosure, as the imaging capsule 150 travels through the small intestine 193, it scans the inner walls and measures the number of CMT and XRF photons received from each radial sector surrounding the imaging capsule 150. Optionally, scanning is triggered by sensing a change in position as detected by a tracking system. The tracking system may be based on a coil 178 or permanent magnet located in the imaging capsule 150 and external receiver 120 worn by the user. Optionally, the tracking system notifies the imaging capsule 150 via a transceiver 177 regarding the motion. In response the imaging capsule 150 scans its surroundings with radiation and returns measurements to the receiver 120. Alternatively, or additionally, the imaging capsule may detect motion with accelerometer 174 or a magnetometer 175 located inside the imaging capsule 150.

In some embodiments of the disclosure, the imaging capsule 150 does not require a contrast agent solution 160 for analysis in the small intestine 193. Instead, in the small intestine 193 only Compton backscattering (CMT) particles are detected to identify the width of the surrounding tissue. Compton backscattering is proportional to the tissue density of the small intestine 193, and the density is influenced by the presence of an inflammation 164 or cancer growth (e.g. a growth/polyp 162).

In another embodiment of the disclosure, the detectors 170 are configured to detect radiation provided by white blood cell (WBC) labelling. Optionally, white blood cells or macrophages from the imaging capsule user are isolated and radio labeled. For example radioisotope labeling can be done with In111, Tc99m, I125, I131 and other radioisotopes which are used in nuclear imaging procedures. The imaging capsule 150 may be also configured to scan independently or just detect radiation from the labelling. Optionally, other types of labelling may be used, for example labeling antibodies targeting inflammation and/or cancer growths with I125, Tc99m, In111 or other isotopes.

Imaging capsule 150 may be administered after labeling the growths/polyps 162 or inflammations 164. As the imaging capsule 150 travels in the small intestine 193 and colon 195, detectors 170 of imaging capsule 150 detect radiation originating from the tissue near it with a specific energy interval. For example in the case of labeling with In111, the x-ray radiation is around 22 Kev which is strongly absorbed by tissue, so only very close by tissue contributes to the detected photons in the imaging capsule 150. Additionally, the imaging capsule 150 may be continually tracked by the tracking system worn by the user, for example external receiver 120. Optionally, tracking and position location are required to estimate capsule travel along the small intestine 193 and colon 195, so that the average radiation detection per unit of small intestine length or colon length can be calculated. Position normalization enhances accuracy of the calculation, since the capsule dose not travel at a uniform velocity, and often stops for long durations at certain positions. Without position normalization, locations where the capsule stayed for a long time would appear "hotter" since a larger number of photons will be detected there over a long time. Alternatively, the "hot spots" can be characterized by a count rate which depends on local radiation activity as a function of time. Thus in this case, there is no need for normalization based on position.

In another embodiment of the disclosure, a thermal sensor 173 is placed on the enclosure 185 of imaging capsule 150. The thermal sensor 173 is used to detect changes in local temperature in the gastrointestinal tract. For example while travelling through the small intestine 193 and/or the colon 195. The temperature changes may provide an indication relating to inflamed areas 164. The temperature sensor may be in addition to other sensors for identifying inflamed areas 164.

In some embodiment of the disclosure, imaging capsule 150 includes a compartment 166 for storing medication, which can be dispensed by a controller 168 that is configured to release drugs locally into the small intestine 193 or colon 195 in response to the local detection of inflamed area 164 near the imaging capsule 150. The medication can be used to locally treat the inflamed area 164 such as in the case of Crohn's disease or other inflammations in the small intestine 193 or colon 195. The drugs may include Humira, Remicade, Azathioprine, Mesalamine, Budesonide, Actemra/Ro-Actemra and other drugs, which are normally administered orally or intravenously. Optionally, by administering locally the medication can be provided directly to the inflamed area 164. Likewise a smaller dosage of medication may be used since the medication is administered directly to the inflamed area 164, thus reducing side effects, which are generally correlated to high systemic spread of a medication dosage.

In an embodiment of the disclosure, electrodes 171 are located on enclosure 185 to generate an electrical field for electrophoresis, when locally releasing medication. Electrophoresis enhances delivery of the medication released from the imaging capsule 150 into the tissue of the user at the location of release by charging the electrodes 171 when releasing the medication.

In an embodiment of the disclosure, the sensors described above (e.g. pH sensor 172, thermal sensor 173, accelerometer 174, magnetometer 175, pressure sensor 176) are able to identify an approximate location of the imaging capsule 150, for example in which organ the imaging capsule 150 is located. Optionally, the sensors may identify when entering or exiting a specific organ. Likewise the imaging capsule 150 may include a timer (e.g. in a controller 168) to estimate where the imaging capsule 150 is located within a specific organ, for example how much time has passed after identifying entry into the specific organ. In an embodiment of the disclosure, the imaging capsule 150 estimates approximately when the imaging capsule 150 is in the middle or end of a specific organ (e.g. the small intestine 193 or colon 195) based on typical flow rates of imaging capsules 150 through a specific organ. Alternatively or additionally, the sensors may provide an indication of the location within a specific organ based on sensor measurements, for example based on a change in pressure, temperature, vibration frequency or other measurements.

In an embodiment of the disclosure, imaging capsule 150 includes a power source, for example a battery 155 for powering the sensors to perform the activities described above.

Figure 3:
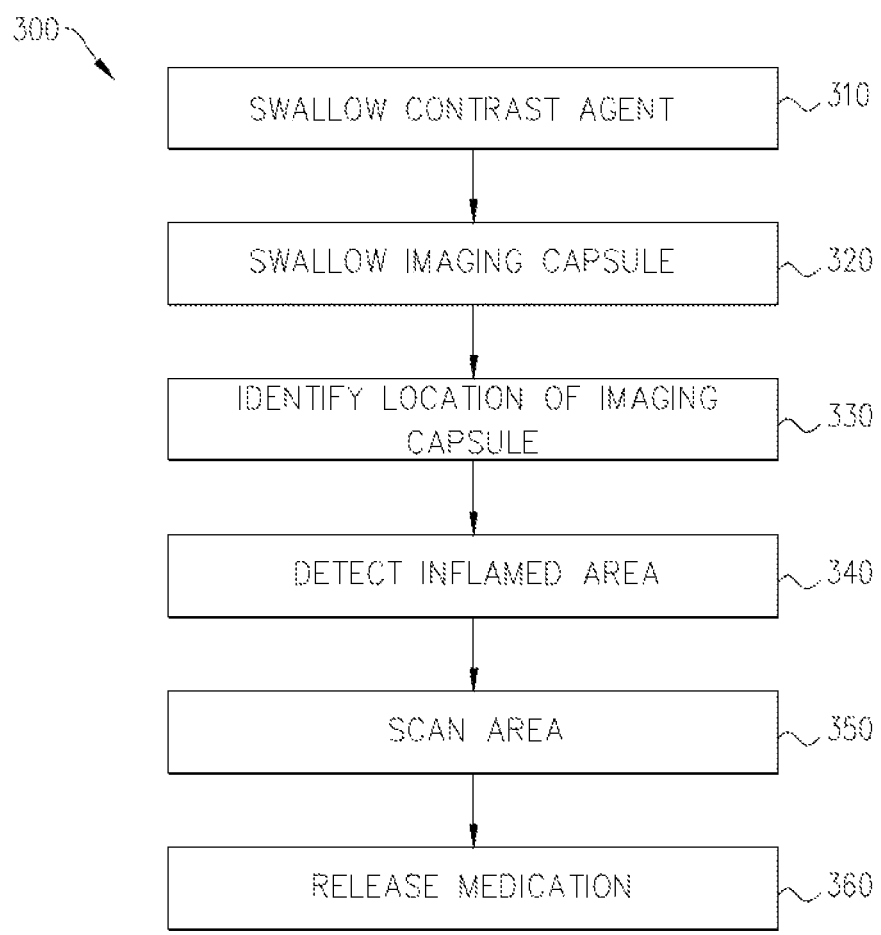
FIG. 3 is a flow diagram of a method of examining a user's small intestine or colon, according to an embodiment of the disclosure.

FIG. 3 is a flow diagram of a method 300 of examining a user's small intestine 193 or colon 195, according to an embodiment of the disclosure. In an embodiment of the disclosure, the user's is generally required to swallow (310) contrast agent 160 to enhance the measurements of X-ray fluorescence in response to the molecules of the contrast agent. After waiting for between about 2-8 hours for the contrast agent to disperse throughout the user's gastrointestinal tract the user swallows (320) the imaging capsule 150. While traversing the gastrointestinal tract the imaging capsule 150 identifies (330) its location, for example, in which organ it is located. Optionally, the organ is detected base on the measurements of one or more sensors, for example a pH sensor 172, thermal sensor 173, accelerometer 174, magnetometer 175 and/or pressure sensor 176. Alternatively or additionally, the organ may be detected by measurements of the detectors 170, which enable for example to determine the distance to the surrounding walls or by identifying an increase or decrease in certain types of radiation (e.g. XRF, CMT).

Optionally, when reaching the small intestine 193 or colon 195 the imaging capsule 150 attempts to detect (340) inflamed areas 164 due to bowel infections or other problems. In some embodiments of the disclosure, imaging capsule 150 detects the inflamed area based on the measurements of detector 170, for example a local increase in the XRF count or decrease in CMT count or detection of radiation from labeled white blood cells (WBC) or other type of radiation labelling.

In an embodiment of the disclosure, upon detecting an inflamed area the imaging capsule 150 can scan (350) the area with radiation to form an image 180 of the inflamed area 164. Alternatively or additionally, imaging capsule 150 may release (360) medication at the inflamed area 164. In some embodiments of the disclosure, imaging capsule 150 may scan and release medication in response to a request from external receiver 120, which is tracking the motion of the imaging capsule 150 and identifies when the imaging capsule 150 reaches a desired location.

In an embodiment of the disclosure, a user may use a series of imaging capsules 150 (e.g. once every few days) to evaluate the user's medical situation and/or release medication. For example each capsule may identify the inflamed area 164, take images 180 and release medication. Alternatively or additionally, each imaging capsule 150 may be programmed to identify a specific organ, then take images and/or release medication in the identified organ.

In some embodiments of the disclosure, imaging capsule 150 may record coordinates of an inflamed area 164 (e.g. based on a tracking system) and transmit the coordinates to the receiver 120. The same receiver 120 may be used with future imaging capsules 150 by the same user, for example when the inflamed area 164 is not labeled. Optionally, the receiver 120 will provide the coordinates to the future imaging capsules 150 so that the imaging capsule can directly locate the inflamed area 164 and take images 180 or deliver medication even if the inflamed area 164 is already cured and not identifiable by an inflammation or labelling.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

We claim:

1. An imaging capsule, comprising:
   a radiation source;
   a collimator that provides a collimated beam from the radiation source;
   at least one detector configured to detect particles resulting from X-ray fluorescence and/or Compton backscattering in response to the collimated beam to reconstruct images of a user's gastrointestinal tract;
   wherein the imaging capsule is configured to identify whether a specific area is an inflamed area, within the user's gastrointestinal tract, based on a count of the detected particles resulting from the Compton backscattering and initiate actions responsive to detecting the inflamed area.

2. The imaging capsule of claim 1, wherein the imaging capsule is further configured to identify the inflamed area based on detecting radiation from radioactively white blood cell labeled tissue at the inflamed area.

3. The imaging capsule of claim 1, wherein the initiated actions include releasing medication responsive to detecting the inflamed area.

4. The imaging capsule of claim 1, wherein the initiated actions include taking images of the identified area.

5. The imaging capsule of claim 1, wherein the imaging capsule further includes one or more sensors configured to identify an approximate location of the imaging capsule.

6. The imaging capsule of claim 5, wherein the approximate location includes identifying an organ in which the imaging capsule is located.

7. The imaging capsule of claim 5, wherein the one or more sensors include a pH sensor or a temperature sensor.

8. The imaging capsule of claim 5, wherein the one or more sensors include a pressure sensor or accelerometer.

9. The imaging capsule of claim 1, wherein the detected particles are used to identify an approximate location of the imaging capsule based on a distance to walls surrounding the imaging capsule.

10. The imaging capsule of claim 1, wherein the detected particles are used to identify an approximate location of the imaging capsule based on an increase or decrease in particles resulting from X-ray fluorescence.

11. The imaging capsule of claim 1, wherein the imaging capsule is configured to receive coordinates from an external recorder that recorded coordinates from a previously used imaging capsule; and release medication or form images at a location designated by the coordinates.

12. The imaging capsule of claim 1, wherein the imaging capsule is configured to detect the inflamed area based on Compton backscattering counts, which are proportional to a density of surrounding tissue.

13. A method of using an imaging capsule, comprising:
    receiving the imaging capsule, including a radiation source within a collimator, which provides a collimated beam from the radiation source, and further includes a detector configured to detect particles resulting from X-ray fluorescence and/or Compton backscattering in response to the collimated beam;
    identifying whether a specific area is an inflamed area, within a user's gastrointestinal tract, based on a count of the detected particles resulting from the Compton backscattering; and
    initiating actions responsive to detecting the inflamed area.

14. The method of claim 13, wherein the imaging capsule is further configured to identify the inflamed area based on detecting radiation from radioactively white blood cell labeled tissue at the inflamed area.

15. The method of claim 13, wherein the initiated actions include releasing medication responsive to detecting the inflamed area.

16. The method of claim 13, wherein the initiated actions include taking images of the identified area.

17. The method of claim 13, wherein the imaging capsule further includes one or more sensors configured to identify an approximate location of the imaging capsule.

18. The method of claim 17, wherein the approximate location includes identifying an organ in which the imaging capsule is located.

19. The method of claim 17, wherein the one or more sensors include a pH sensor or a temperature sensor.

\* \* \* \* \*